(12) United States Patent
Calvo et al.

(10) Patent No.: US 6,686,203 B2
(45) Date of Patent: Feb. 3, 2004

(54) HISTOLOGIC VISUALIZATION OF CYANOACRYLATE EMBOLIZATION

(76) Inventors: William J. Calvo, 250 Kettering Dr., Buffalo, NY (US) 14223; Baruch B. Lieber, 1662 Winterberry La., Weston, FL (US) 33327

(*) Notice: Subject to any disclaimer, the term of this patent is extended or adjusted under 35 U.S.C. 154(b) by 31 days.

(21) Appl. No.: 09/950,964

(22) Filed: Sep. 11, 2001

(65) Prior Publication Data

US 2002/0031443 A1 Mar. 14, 2002

Related U.S. Application Data

(60) Provisional application No. 60/231,816, filed on Sep. 11, 2000.

(51) Int. Cl.$^7$ ................................................. G01N 33/48
(52) U.S. Cl. ..................... 436/63; 436/164; 436/172; 422/61; 422/82.05; 422/82.08; 435/40.5; 435/40.52
(58) Field of Search ............... 436/63, 164, 166, 436/172; 422/61, 82.05, 82.08; 435/1.1, 40.5, 40.52

(56) References Cited

U.S. PATENT DOCUMENTS

| | | | |
|---|---|---|---|
| 4,972,837 A | * 11/1990 | Engelstad et al. ........... 120/654 |
| 5,342,645 A | * 8/1994 | Eisele et al. ................ 427/1 |
| 5,348,159 A | 9/1994 | Watkin et al. |
| 5,702,361 A | * 12/1997 | Evans et al. ................ 604/53 |
| 5,871,804 A | * 2/1999 | Wilkinson et al. .......... 427/1 |
| 5,928,627 A | * 7/1999 | Kiefer et al. ............... 424/9.6 |

* cited by examiner

Primary Examiner—Maureen M. Wallenhorst
(74) Attorney, Agent, or Firm—Hodgson Russ LLP

(57) ABSTRACT

A histological staining technique that allows quantification of previously unmeasured parameters involved in surgical arteriovenous malformation (AVM) embolization. The invention allows the evaluation of the polymerization characteristics of various ratios of embolization agents, such as Lipiodol/n-butyl 2-cyanoacrylate (NBCA)/glacial acetic acid (GAA) mixtures, by virtue of a new tissue sample preparation protocol and staining technique. To determine the depth of NBCA penetration within the AVM model and to characterize the polymerization patterns of various mixtures within a model vessel, histologic cross-and longitudinal sections were prepared for microscopy using a new staining method including the use of europium aryl-β-diketone complex and petroleum ether. Paraffin-embedded tissue sections were subjected to the staining protocol to improve differentiation between NBCA and Lipiodol.

22 Claims, 8 Drawing Sheets

HISTOLOGIC VISUALIZATION OF CYANOACRYLATE EMBOLIZATION

CROSS-REFERENCE TO RELATED APPLICATION

Applicant hereby claims priority based on U.S. Provisional Application No. 60/231,816 filed Sep. 11, 2000, entitled "Histologic Visualization of Cyanoacrylate Embolization" which is incorporated herein by reference. This invention was made with government support under grant HL-07765-09 awarded by the NHLBI. The government has certain rights in the invention.

FIELD OF INVENTION

The present invention pertains to a method for histological staining of arteriovenous malformation (AVM) tissue samples in order to quantify parameters of surgical AVM embolization using an europium aryl-β-diketone complex.

BACKGROUND OF THE INVENTION

Arteriovenous malformations (AVMs) are, in most patients, congenital lesions formed by tangled networks of blood vessels. The cause of AVMs is not known, but most AVMs are thought to be due to abnormal development of blood vessels during fetal development. While AVMs can potentially form anywhere in the body, those formed in the brain are particularly problematic.

In normal brain tissue, blood enters through major cerebral arteries, passes through smaller arterioles, and subsequently moves into capillaries. Capillaries are tiny blood vessels that allow blood to deliver necessary oxygen and nutrients to the brain and remove waste products of brain metabolism. Normally, after passing through the capillaries, the blood enters the brain's venous system. When an AVM exists in the brain, blood is shunted directly from the arterial system to the venous system. There is normally a drop in pressure as blood travels from arteries to veins, but when an AVM is present, the rate of blood flow from arteries to veins can be high and the pressure can thus be elevated within the veins. This elevated pressure can contribute to a variety of complications, including stroke, seizures, bleeding, and disruption of the normal function of brain cells near the AVM.

The treatment for AVMs includes a procedure by which an endovascular occlusion of blood flow through these abnormal arteriovenous shunts is intentionally created by physician intervention. This is done by the surgical introduction of an occlusive agent into the AVM to embolize the AVM such that the blood flow through the AVM is impeded and ultimately rerouted to the venous system.

Over the past several years, many different occlusive agents have been tested in a variety of endovascular treatments. Liquid adhesive polymers (glues) which rapidly solidify have been used for such procedures as bone grafting, skin incision repair, dental cements, and as embolic agents. More specifically, various derivatives of alkyl-cyanoacrylates have been demonstrated to provide highly favorable results when compared to other embolic agents.

The most common embolic agent used currently is n-butyl 2-cyanoacrylate (NBCA) or enbucrilate. In order to control the polymerization time of NBCA, as well as to opacify the mixture for angiographic visualization, an iodized poppy-seed oil-based contrast agent (Lipiodol) is added to the NBCA. Glacial acetic acid (GAA) is also used to delay the polymerization time further by decreasing the pH of the mixture.

Research efforts have focused on finding ways to better quantify the hemodynamic parameters, such as pressure, flow and NBCA injection pressure involved in AVM embolization, thus improving the reproducibility of successful outcomes for patients. An understanding of the complex and variable anatomy of AVMs is essential prior to treatment, but knowledge of the velocities and transit times of blood through the AVM nidus (arteriovenous fistulae network) is equally as essential for successful endovascular intervention. Both physical skill as well as precise prediction of embolic agent behavior within the vessels is needed in order to avoid non-optimal glue casting outcomes.

During injection of the NBCA, polymerization of the NBCA-Lipiodol mixture exactly within the AVM nidus is crucial. If proximal feeding arteries are occluded without NBCA penetration into the nidus, revascularization of the AVM will occur. Delayed polymerization and occlusion of distal draining veins may result in serious complications such as hemorrhage, emboli, stroke or death.

Since the hemodynamic parameters involved have not been accurately quantified to date, NBCA embolization of AVMs is still considered a high-risk procedure. Improved characterization of embolization hemodynamics necessitates analysis of how deep NBCA penetrates into the AVM nidus. In addition, interaction of the mixture (NBCA and Lipiodol) with the vessel wall and polymerization rates must be examined. Thus, there is a need for better visualization techniques of embolized AVM tissue samples so that such parameters can be quantified.

SUMMARY OF THE INVENTION

The present invention comprises a new histological staining technique that allows quantification of previously unmeasured parameters involved in surgical AVM embolization. The invention allows the evaluation of the polymerization characteristics of various ratios of embolization agents, such as Lipiodol/NBCA/glacial acetic acid (GAA) mixtures, by virtue of a new tissue sample preparation protocol and staining technique.

To determine the depth of NBCA penetration within the AVM model and to characterize the polymerization patterns of various mixtures within a model vessel, histologic cross- and longitudinal sections were prepared for microscopy using a new staining method comprising the use of a europium aryl-β-diketone complex and petroleum ether. Paraffin-embedded tissue sections were subjected to the staining protocol to improve differentiation between NBCA and Lipiodol. Quantification of NBCA and Lipiodol within the lumen of rete cross-sections was accomplished using image analysis software to determine percent luminal area occluded by embolization. Upon application of europium tris(thenoyltrifluoroacetone) or TEC, intense europium fluorescence was seen when the tissue samples were excited by low-power ultraviolet light. The area of europium intensity within the lumen corresponded to NBCA concentration, and addition of GAA aided the NBCA distribution throughout the lumen without affecting fluorescence intensity. The invention demonstrates that NBCA can be easily differentiated from Lipiodol and quantification of previously unmeasured parameters can be readily performed on these sections because of the improved tissue sample staining technique.

The invention also relates to a kit for quantifying n-butyl 2-cyanoacrylate (NBCA) within treated tissues that includes europium aryl-β-diketone complex, petroleum ether and methanol, each in containers holding predetermined amounts of the reagents.

DESCRIPTION OF THE PREFERRED EMBODIMENTS

EXAMPLE 1

Figure 1:
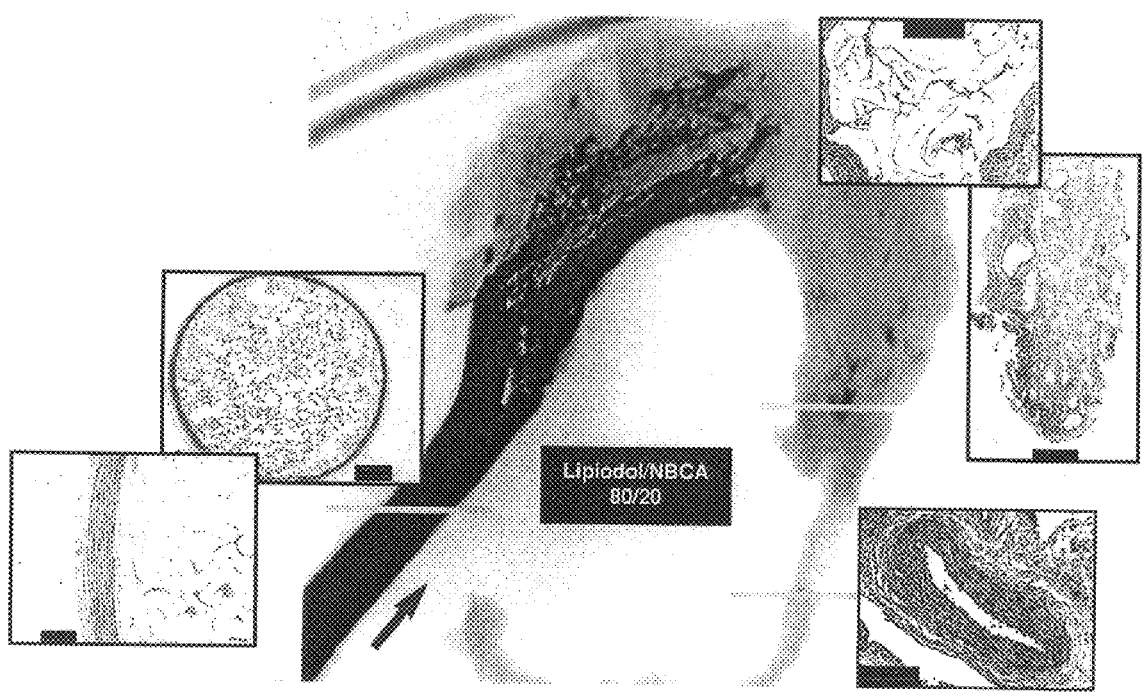
FIG. 1. High-resolution radiogram and histology of post-embolized rete for chronic AVM model using an 80:20 Lipiodol:NBCA ratio (volume %). Note red arrow indicates site and direction of glue injection during experiment. Three locations along the rete were selected for cross-sections as indicated by the yellow lines. The insets represent the results of tissue staining at each indicated location. Scale bars are (clockwise, from upper right) 100, 2000, 100, 100, and 500 µm.

Tissue used in this embodiment consisted of swine retia harvested from acute and chronic AVM model studies. Dissected retia for vessel histology were fixed in fresh buffered 3% formaldehyde for 2 hours (4° C.), rinsed, dehydrated, paraffin-embedded, and radially sectioned (5 µm) onto poly-L-lysine-coated slides. Samples were obtained radially at predetermined angles spanning the entire rete from left to right of the ascending pharyngeal artery. Sections chosen for color staining were processed with the lipid dye Oil-Red-O, according to routine protocols. Sections chosen for fluorescent staining were processed with a working solution of europium tris(thenoyltrifluoroacetone) or TEC. A 200-mL stock solution of TEC was first prepared by dissolving 0.25 g of europium trichloride hexahydrate in 100 mL absolute ethanol and combining this solution with 0.5 g of thenoyltrifluoroacetone dissolved in 100 mL of petroleum ether. The two solutions were combined by stirring for 5 minutes. Next, a working solution (100 mL) of TEC was prepared with 50 mL of stock solution added to 25 mL of petroleum ether and 25 mL of absolute ethanol. Tissue samples chosen for TEC staining were processed in the following manner: three Coplin jars were arranged in sequence, with the first containing petroleum ether, the second containing TEC, and the third containing 100% methanol. A slide containing the embolized tissue sample was gently placed into the first jar for 1 minute to dissolve the paraffin completely. Next, the slide was removed and immediately transferred to the second jar (TEC) for 1 minute. Finally, the slide was removed and immediately transferred to the third jar (100% methanol) for 1 minute. The slide was then removed, air-dried, and mounted with 50% glycerol for subsequent microscopic examination.

All samples were examined at the Confocal Microscopy and 3-D Imaging Core Facility operated by the State University of New York at Buffalo. A Nikon FXA Automated Fluorescence Microscopy System equipped with 35 mm and 4-in×5-in film cameras was used. The system also included a high-resolution, monochrome, computer-controlled, cooled CCD camera for fluorescence and color-bright field imaging. A DAPI filter cube was used for imaging samples under fluorescence. The excitation wavelength for TEC was at 365 nm, and the emission wave length was at 614 nm. Microscope images were photographed with Kodak Elite Chrome color slide film (400 ASA). Measurements of NBCA and Lipiodol within the lumen of rete cross-sections were accomplished by first tracing (with a computer mouse) the digitized images of the sections by using NIH Image software (Version 1.61) and subsequently determining percent luminal area as a ratio of corresponding pixel summation. Measurements were made in triplicate and were obtained from three different observers performing the tracing. High-resolution radiograms were obtained for various post-embolized harvested retia in order to delineate the extent of NBCA penetration.

Figure 2:
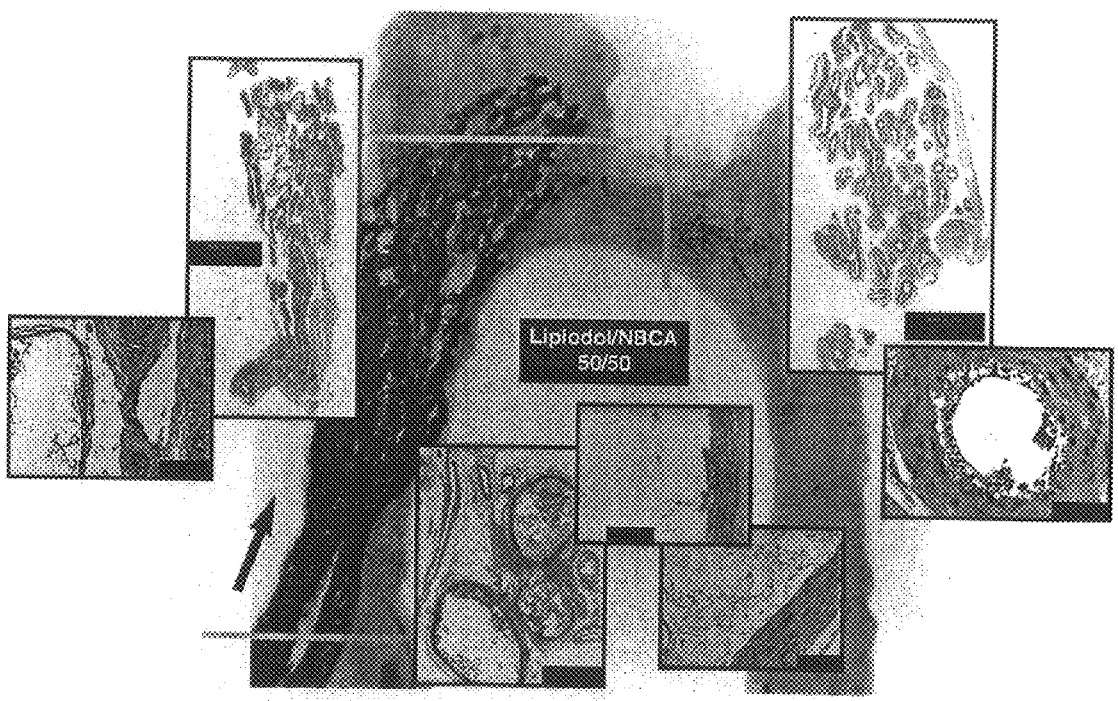
FIG. 2. High-resolution radiogram and histology of post-embolized rete for chronic AVM model using a 50:50 Lipiodol:NBCA ratio (volume %). Note red arrow indicates site and direction of glue injection during experiment. Three locations along the rete were selected for cross-sections as indicated by the yellow lines. The insets represent the results of tissue staining at each indicated location. Scale bars are (clockwise, from upper right) 1000, 50, 100, 100, 1000, 100 and 2000 µm.
Figure 3:
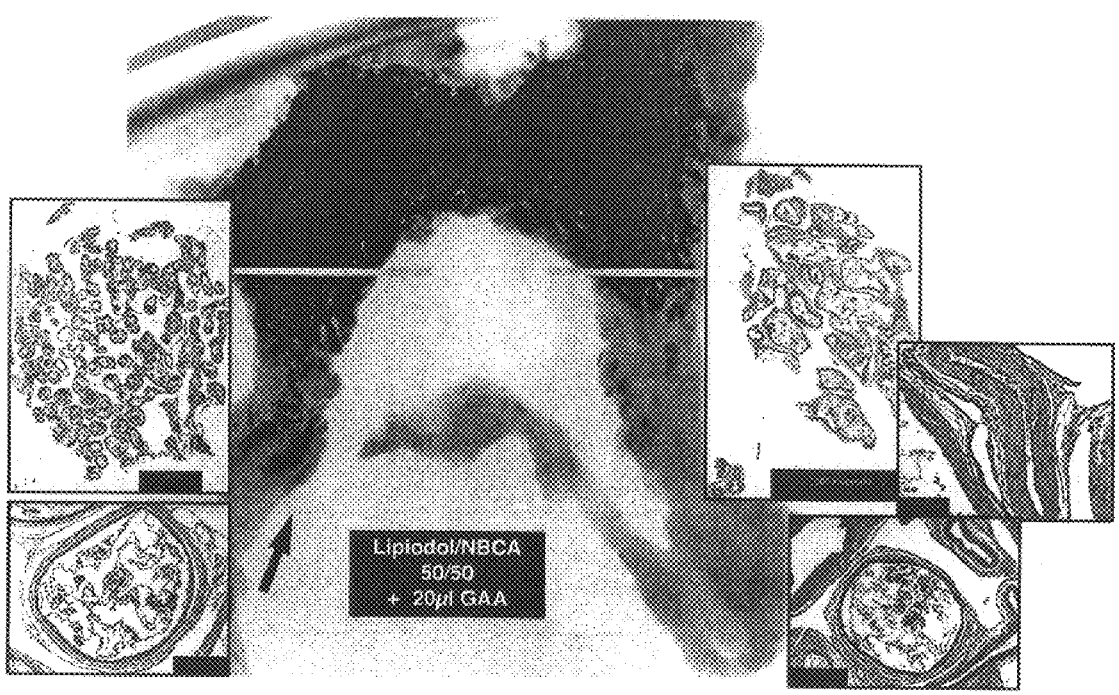
FIG. 3. High-resolution radiogram and histology of post-embolized rete for chronic AVM model using a 50:50 Lipiodol:NBCA ratio (volume %) with 20 microliters of glacial acetic acid (GAA) added. Note red arrow indicates site and direction of glue injection during experiment. Two locations along the rete were selected for cross-sections as indicated by the yellow lines. The insets represent the results of tissue staining at each indicated location. Magnifications are (clockwise, from upper right) 2000, 100, 200, 200, and 2000 µm.

Using the chronic AVM model, an 80:20 Lipiodol:NBCA ratio yielded proximal embolization with incomplete and inhomogeneous penetration of the rete (FIG. 1). In addition, there appeared to be sputtered penetration beyond the midplane of the rete. Incomplete and inhomogeneous penetration of the rete was also the case when the ratio of Lipiodol:NBCA was changed to 50:50 (FIG. 2). A more proximal occlusion than for the 80:20 case can be seen and inhomogeneity can be seen by the presence of voids along the injection path. Upon addition of 20 mL of GAA to a 50:50 mixture of Lipiodol:NBCA(1.8 mL total volume), a much more homogeneous penetration of the mixture was seen, as illustrated by an increased amount of radiopaque material within the contralateral ascending pharyngeal artery(FIG. 3).

Embolized tissue cross-sections were evaluated histologically with respect to the degree of differentiation between NBCA and the surrounding tissue. This evaluation was done for all sections processed with the color stain Oil-Red-O. Representative samples are shown in FIGS. 1 through 3, wherein the yellow lines show various designated positions selected along the rete. At each position, the corresponding tissue cross-section is shown as stained with Oil-Red-O (inset). Because this lipid dye depends on the oleophyllic properties of NBCA, regions of tissue containing NBCA manifest a pink-red color. However, two difficulties arose with using this type of color stain. First, it became difficult to distinguish between tissue, Lipiodol, and any residual blood/blood products. Secondly, various shades of pink-red were present in the sections as shown in FIGS. 1 through 3. It was not possible to determine whether these different shades of color were because of non-uniformity in tissue staining or if color intensity was directly proportional to the concentration of NBCA within a particular region of tissue. Owing to these qualitative difficulties, a more quantitative method for determining NBCA concentration within embolized tissue was sought using europium fluorescence.

EXAMPLE 2

Several control experiments were performed first in order to examine the selective binding of europium to NBCA within a tissue section. Staining experiments were designed to examine europium binding to NBCA solely on the presence (or absence) of a fluorescent signal when sections were exposed to UV light under microscopy. This binding was examined under both dried and undried conditions. The dried state simulated actual tissue preparation conditions, because NBCA rapidly polymerizes after injection into the vasculature. Application of europium to undried samples was used to determine if NBCA polymerization affects fluorescence to any degree. In order to examine europium binding to NBCA in a dried state, 15 μL of NBCA were allowed to air-dry onto a glass slide 20 minutes prior to application of 15 μL TEC onto the NBCA. To examine NBCA in an undried state, TEC was immediately applied onto the NBCA droplet. The volume (15 μL) for both NBCA and TEC was determined after numerous trials to be an optimal volume for microscopic slide preparation. These control experiments subsequently demonstrated that europium did bind to NBCA. Interestingly, binding was observed for both undried and dried states of NBCA. Control experiments were also performed to determine any europium binding to Lipiodol. When a 15-μL volume of Lipiodol was viewed under UV light with and without europium staining, no distinction could be made. Further control experiments were designed to determine europium's binding behavior to the mixture of Lipiodol and NBCA. When staining both with and without europium, it was found that fluorescence was seen exclusively in the sample containing europium. The end result of these control experiments led to the observation that europium selectively binds only to the NBCA in the NBCA-Lipiodol mixture.

Figure 4:
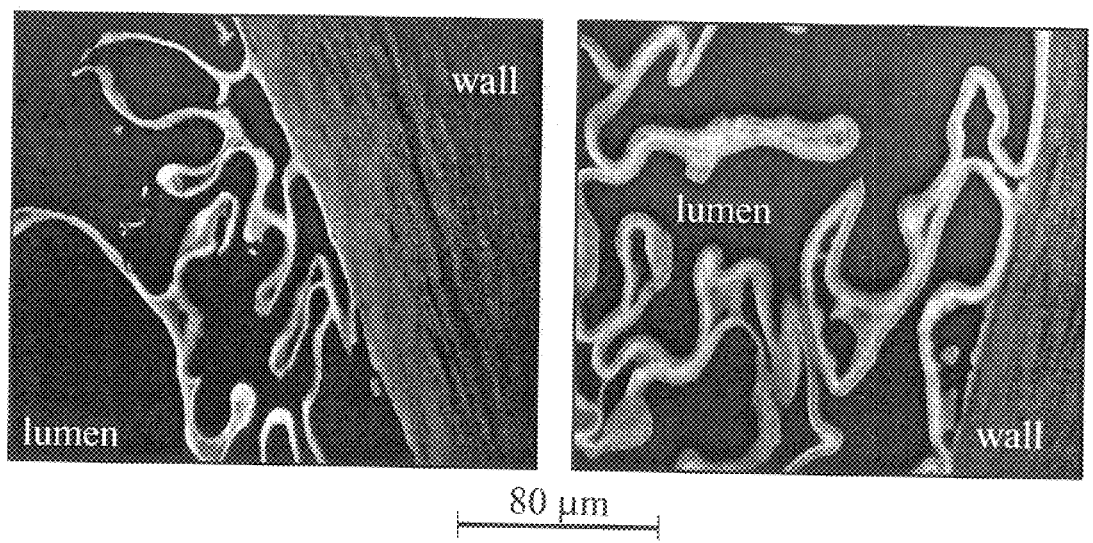
FIG. 4. Paraffin-embedded rete tissue after europium emission observed at 614 nm for an 80:20 Lipiodol:NBCA ratio. Cross-sections were processed in the absence of TEC (left panel) and with TEC (right panel). Positions of the vessel wall and lumen are indicated. Scale bar distance is as shown.
Figure 5:
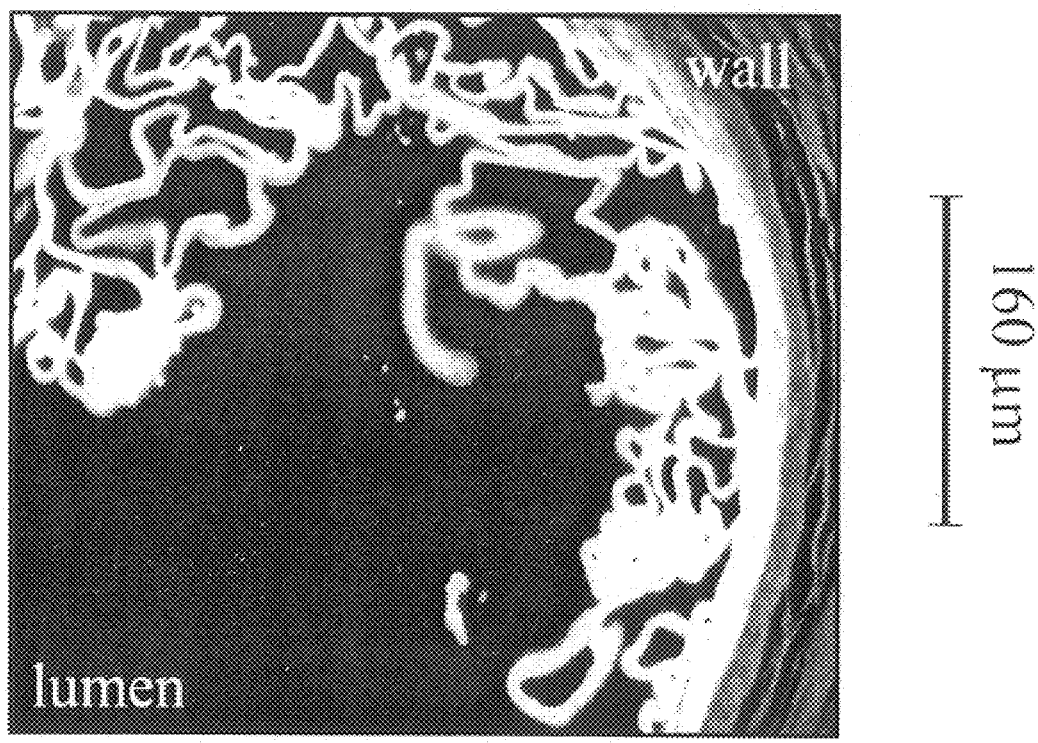
FIG. 5. Paraffin-embedded rete tissue after europium emission observed at 614 nm for an 80:20 Lipiodol:NBCA ratio. Cross-section was processed with TEC. Positions of the vessel wall and lumen are indicated. Scale bar distance is as shown.

When paraffin-embedded cross-sections of rete tissue were examined under UV light, several interesting results were observed. FIG. 4 shows a section through a rete embolized with a Lipiodol:NBCA mixture of 80:20. The left panel shows that an exogenous material (presumably polymerized NBCA) took the form of irregular, interwoven folds within the lumen, and that portions of this material adhered to the vessel wall. When tissue was processed with europium (TEC), an intense fluorescence was seen (right panel), which was absent in the europium-free tissue (left panel). This result suggests that a europium tris chelate can be used to target NBCA in embolized tissue sections. The NBCA fluorescence was seen as orange in color, appearing as a distinctly intense band of uniform thickness and coursing the same irregular, interwoven pattern as that determined to be polymerized NBCA (left panel of FIG. 4). Lipiodol, in contrast, appeared dark (or opaque) in FIG. 4 (both panels). This was expected, because the control experiments demonstrated that adding europium to Lipiodol did not induce any fluorescence. Finally, material (presumably blood and/or blood products) was observed within some of the folds formed by the polymerized NBCA. Continuous flow during embolization entraps blood and/or blood products upon polymerization of NBCA. As seen in a lower magnification photograph for the 80:20 case (FIG. 5), regions within the vessel lumen can be readily distinguished from Lipiodol because of the europium fluorescence. FIG. 5 also illustrates more clearly that NBCA tends to adhere to the vessel wall.

Figure 6:
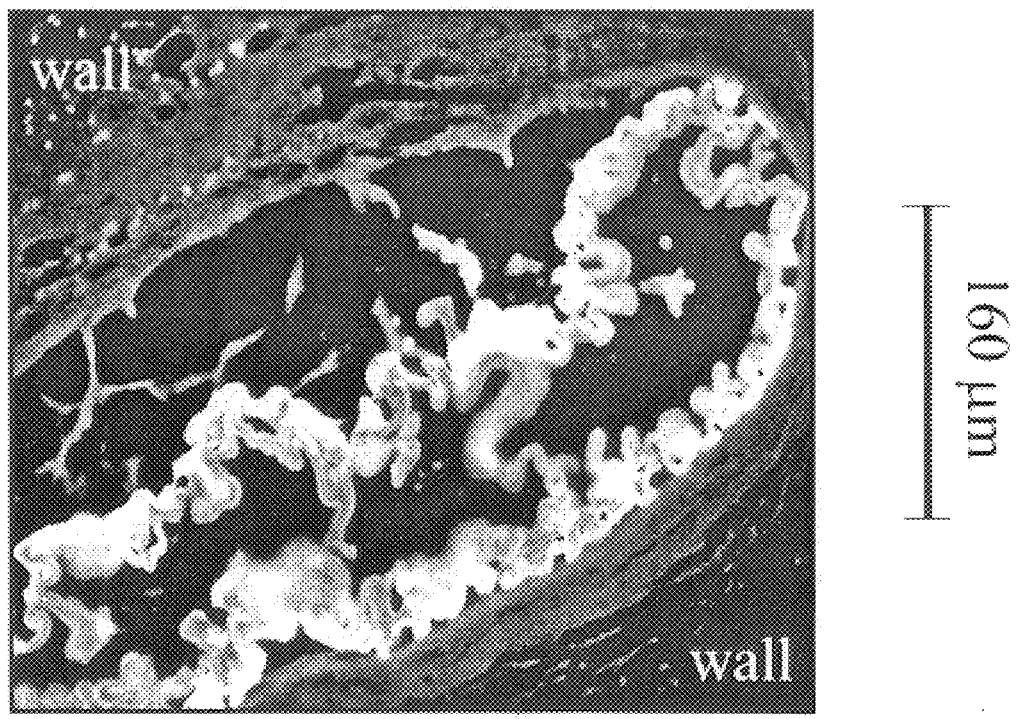
FIG. 6. Paraffin-embedded rete tissue cross-section after TEC-processing and upon europium emission observed at 614 nm for a 50:50 Lipiodol:NBCA ratio. Position of the vessel wall is indicated. Scale bar distance is as shown.
Figure 7:
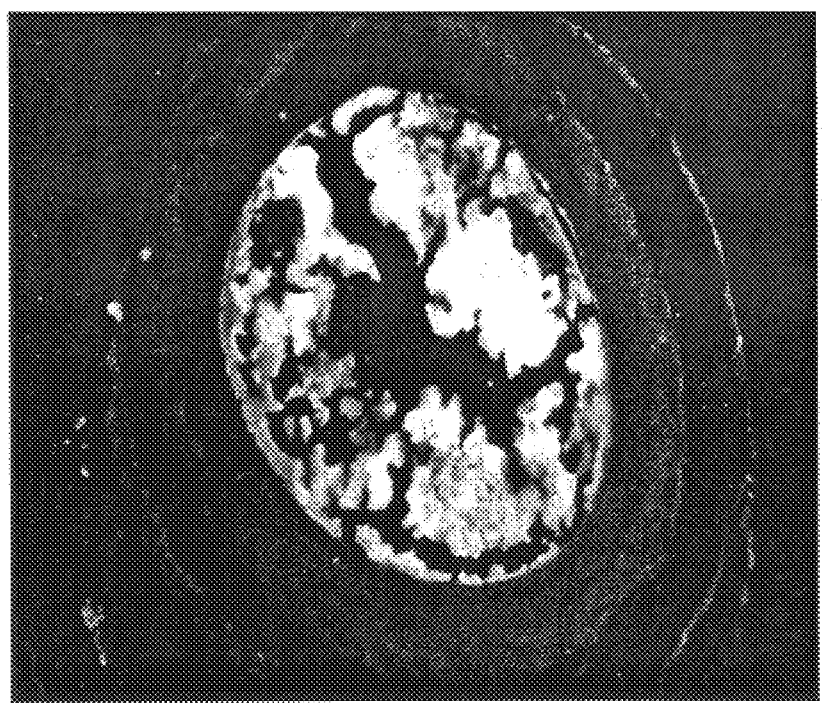
FIG. 7. Paraffin-embedded rete tissue cross-section after TEC-processing and upon europium emission observed at 614 nm for a 50:50 Lipiodol:NBCA ratio (plus 20 microliters of acetic acid). Scale bar distance is as shown.

When the ratio of Lipiodol:NBCA was changed from 80:20 to 50:50, it was expected that NBCA would be present within the lumen at a higher concentration. Cross-sections processed with europium confirmed this prediction (see FIGS. 5 and 6). The higher concentration of NBCA produced a thicker band of europium fluorescence (FIG. 6), whereas the lower concentration showed a narrower band (FIG. 5). This demonstrates that, within the cross section of vessel lumen, the area of europium intensity corresponds to NBCA concentration. The tissue section in FIG. 6 also showed some stripping of the endothelium. FIG. 7 shows a section through a blood vessel from a rete that was embolized with a mixture composed of 0.9 mL of Lipiodol and 0.9 mL of NBCA, with the addition of 20 mL GAA (intended to delay NBCA polymerization). Comparison of FIG. 6 with FIG. 7 demonstrates that the addition of GAA facilitates NBCA distribution throughout the lumen, preventing its concentration in a narrow band adjacent to the wall. However, the addition of such a small quantity of GAA had no effect on the intensity of fluorescence.

Histopathologic studies were performed on autopsy tissue of swine rete. Both acute and chronic animal models were used in these studies to create conditions that better mimic human AVMS. Histologic comparison of the chronic versus acute model can help determine if vascular wall modifications (such as ectasia) could be induced experimentally through, for example, weakening of the vascular wall or the creation of collagen voids. Radiograms of excised embolized retia (FIGS. 1 through 3) indicate the depth of penetration of the Lipiodol-NBCA mixture. However, the histologic results with Oil-Red-O (as seen by the various insets in each figure) only serve to qualitatively confirm these radiographic results.

Figure 8:
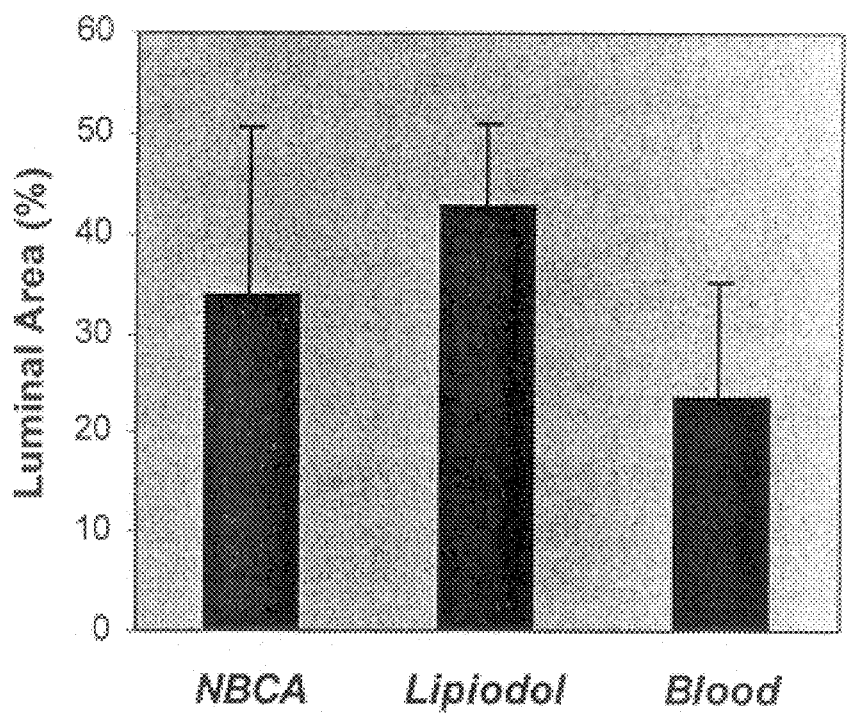
FIG. 8. Distribution of the various components comprising the glue-oil mixture for an NBCA:Lipiodol ratio of 50:50 (with 20 microliters of glacial acetic acid added) as measured by image analysis of the TEC-processed tissue cross-section.

In order to quantify the degree of occlusion by NBCA within the vessel, europium staining of tissue was used. The results of the experiments shown in FIGS. 4 through 7 indicate that intense fluorescence was seen when a europium tris chelate(aryl-β-diketone complex) was excited by UV light. Minimal background fluorescence was observed when examining the tissue cross-sections. The excellent contrast provided by TEC (FIG. 4, right panel) was not affected by the enhanced autofluorescence normally caused by formaldehyde fixative (FIG. 4, left panel). A quantitative determination using image analysis was made for the 50:50 (plus 20 mL GAA) mixture seen in FIG. 7. This subsequently allowed for calculation as to what (in terms of area) constituted NBCA (and alternatively, Lipiodol) within the cross-section. The result of this analysis (FIG. 8) showed that, within statistical error, calculated NBCA and Lipiodol concentrations matched the respective concentrations initially used during the actual experiment. Histologic examination of the stained retia (using either Oil-Red-O or europium) revealed that, for both stains, NBCA does not fill the entire lumen of the vessel. Further examination of Lipiodol in the lumen also shows different visual characteristics with the two staining techniques.

It appears that pockets of NBCA surrounded by Lipiodol are formed with Oil-Red-O staining. Conversely, when europium staining is used, it seems that pockets of Lipiodol encapsulated by NBCA are formed. Because this improved staining technique allows for better visualization of the Lipiodol-NBCA interface, it is therefore hypothesized that Lipiodol becomes sequestered by the NBCA upon polymerization. The oil, visually distinguished by spaces within the lumen, is usually seen within the inside diameter of the section, whereas the NBCA is situated along the periphery. From a hemodynamic perspective, as the injected embolic mixture travels through the vessel, the velocity is greatest at the centerline and zero near the vessel wall (if a noslip boundary condition is assumed). This phenomenon facilitates NBCA polymerization near the vessel wall. It also explains the histologic results, which show that NBCA has a higher tendency to adhere to the vessel wall. Only small amounts of NBCA are observed in the vicinity of the vessel centerline because, intuitively, NBCA would be more likely to be displaced toward the vessel wall as flow progresses (FIGS. 5 through 7). The new histological staining technique has allowed the inventors to recommend a wedge position of the micro catheter during NBCA injection or asystole, which ensures a flow reduction or arrest and a more homogeneous distribution of the glue within the nidus.

To our knowledge, this is the first study using europium in the development of a fluorescent staining technique for post-embolized cerebrovascular tissue. The invention allows europium fluorescence as a technique for distinguishing NBCA from Lipiodol and blood/blood products in embolized tissue.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A method for staining and imaging n-butyl 2-cyanoacrylate (NBCA) in tissues, comprising:
    preparing a histological tissue sample from tissue that has been treated with n-butyl 2-cyanoacrylate (NBCA);
    staining the histological tissue sample with europium aryl-β-diketone complex;
    exciting the stained tissue sample with ultraviolet light; and,
    imaging the excited, stained tissue sample.

2. The method of claim 1, wherein the europium aryl-β-diketone complex comprises europium tris (thenoyltrifluoroacetone).

3. The method of claim 2, further comprising preparing a stock solution of europium tris(thenoyltrifluoroacetone) by dissolving europium trichloride hexahydrate in ethanol to form a first solution and combining the first solution with a second solution formed by dissolving thenoyltrifluoroacetone in petroleum ether.

4. The method of claim 3, further comprising preparing the europium tris(thenoyltrifluoroacetone) by adding the stock solution to petroleum ether and ethanol.

5. The method of claim 1, wherein an excitation wavelength of the ultraviolet light is approximately 365 nm.

6. The method of claim 1, wherein an emission wavelength from the europium aryl-β-diketone complex is approximately 614 nm.

7. The method of claim 1 further comprising immersing the sample in petroleum ether prior to staining.

8. The method of claim 1 further comprising immersing the sample in methanol prior to exciting the stained sample with ultraviolet light.

9. The method of claim 1, wherein the tissue sample comprises an embolized arteriovenous malformation (AVM).

10. A method for staining and imaging n-butyl 2-cyanoacrylate (NBCA) in tissue, comprising:
    preparing a slide of a histological tissue sample from tissue that has been treated with a glue mixture comprising n-butyl 2-cyanoacrylate (NBCA);
    immersing the slide in petroleum ether to remove a wax-like substance that the tissue is embedded in;
    immersing the slide in a europium aryl-β-diketone complex to stain the tissue sample;
    immersing the slide in methanol;
    exciting the stained tissue sample with ultraviolet light; and,
    imaging the excited tissue sample.

11. The method of claim 10, wherein the europium aryl-β-diketone complex comprises europium tris (thenoyltrifluoroacetone).

12. The method of claim 11, further comprising preparing a stock solution of europium tris(thenoyltrifluoroacetone) by dissolving europium trichloride hexahydrate in ethanol to form a first solution and combining the first solution with a second solution formed by dissolving thenoyltrifluoroacetone in petroleum ether.

13. The method of claim 12, wherein the europium trichloride hexahydrate is dissolved in the ethanol at a ratio of approximately 0.25 g/100 ml.

14. The method of claim 13, wherein the europium tris(thenoyltrifluoroacetone) is produced by adding the stock solution to petroleum ether and ethanol in a ratio of approximately 2:1:1 respectively.

15. The method of claim 12, wherein the thenoyltrifluoroacetone is dissolved in the petroleum ether at a ratio of approximately 0.5 g/100 ml.

16. The method of claim 15, wherein the europium tris(thenoyltrifluoroacetone) is produced by adding the stock solution to petroleum ether and ethanol in a ratio of approximately 2:1:1 respectively.

17. The method of claim 12, wherein the europium tris(thenoyltrifluoroacetone) is produced by adding the stock solution to petroleum ether and ethanol in a ratio of approximately 2:1:1 respectively.

18. The method of claim 11, wherein an emission wavelength of the europium tris(thenoyltrifluoroacetone) is approximately 614 nm.

19. The method of claim 10, wherein an excitation wavelength for the ultraviolet light is approximately 365 nm.

20. A kit for quantifying n-butyl 2-cyanoacrylate (NBCA) within treated tissues, comprising europium aryl-β-diketone complex, petroleum ether, methanol and packaging therefor.

21. The kit of claim 20, further comprising three containers for holding predetermined amounts of the europium aryl-β-diketone complex, petroleum ether, and methanol.

22. The kit of claim 20, wherein the europium aryl-β-diketone complex comprises europium tris (thenoyltrifluoroacetone).

* * * * *